United States Patent [19]
Lee et al.

[11] Patent Number: 5,886,180
[45] Date of Patent: Mar. 23, 1999

[54] 25-METHYLENE AND 24-25 -EPOXY MARCFORTINES AND PARAHERQUAMIDES

[75] Inventors: Byung H. Lee; Michael F. Clothier, both of Kalamazoo, Mich.

[73] Assignee: Pharmacia & Upjohn Company, Kalamazoo, Mich.

[21] Appl. No.: 924,347

[22] Filed: Sep. 5, 1997

Related U.S. Application Data

[60] Provisional application No. 60/025,983, Sep. 9, 1996.
[51] Int. Cl.$^6$ .................................................. C07D 241/36
[52] U.S. Cl. ............................................................ 544/341
[58] Field of Search .............................. 544/341; 514/250

[56] References Cited

U.S. PATENT DOCUMENTS

| | | | |
|---|---|---|---|
| 4,866,060 | 9/1989 | Mrozik | 514/250 |
| 4,873,247 | 10/1989 | Goegelman et al. | 514/257 |
| 4,923,867 | 5/1990 | Blizzard et al. | 514/250 |
| 4,978,656 | 12/1990 | Blizzard et la. | 514/63 |
| 5,703,078 | 12/1997 | Lee | 514/250 |

FOREIGN PATENT DOCUMENTS

| | | |
|---|---|---|
| 301742-A | 2/1989 | European Pat. Off. |
| 390532-A | 10/1990 | European Pat. Off. |
| WO 91/09961 | 7/1991 | WIPO |
| 92/00300 | 1/1992 | WIPO |
| WO 92/00300 | 1/1992 | WIPO |
| WO 92/22555 | 12/1992 | WIPO |
| WO 94/29319 | 12/1994 | WIPO |

OTHER PUBLICATIONS

*J. Chem. Soc. Chem. Communications*, pp. 601–602 (1980).
*Tetrahedron Letters*, 22, pp. 1977–1980 (1980).
*Tetrahedron Letters*, 22, pp. 135–136 (1981).
*J. of Antibiotics*, 44, pp. 492–497 (1991).
*J. of Antibiotics*, 43, pp. 1380–1386 (1990).
*J. Am. Chem. Soc.*, 118, 3, pp. 557–579 (1996).
*J. Am. Chem. Soc.*, 115, 20, pp. 9323–9324 (1993).

*Primary Examiner*—Evelyn Huang
*Attorney, Agent, or Firm*—Bruce Stein

[57] ABSTRACT

The present invention are marefortines and paraherquamides where the 7-member oxygenated ring has been modified to produce 25-methylene compounds (VII) and 24,25-epoxy compounds (VIII) all of which are useful as antiparasitic agents against endo and ecto parasites, particularly helminths and arthropods.

14 Claims, No Drawings

25-METHYLENE AND 24-25-EPOXY MARCFORTINES AND PARAHERQUAMIDES

CROSS-REFERENCE TO RELATED APPLICATIONS

This application claims the benefit of U.S. provisional application Ser. No. 60/025,983 filed 9 Sep. 1996, under 35 USC §119(e)(i).

BACKGROUND OF THE INVENTION

1. Field of the Invention

The present invention is (substituted) 25-methylene and 24,25-epoxy marcfortines and paraherquamides which are useful as antiparasitic agents.

2. Description of the Related Art

The marcfortines are known compounds, see *Journal of the Chemical Society Chemical Communications*, 601–602 (1980) for Marcfortine A and *Tetrahedron Letters*, 22, 1977–1980 (1981) for Marefortines B and C. These compounds are fungal metabolites of *Penicillium roqueforti*. The marcfortines are structurally related to the paraherquamides which are also known compounds.

The paraherquamides are disclosed in *Tetrahedron Letters*, 22, 135–136 (1981), and *Journal of Antibiotics*, 44, 492–497 (1991). U.S. Pat. Nos. 4,866,060 and 4,923,867 disclose the use of the marcfortines A, B, and C, and certain derivatives thereof as useful for the treatment and prevention of parasitic diseases in animals.

WO 92/22555 (published 23 Dec. 1992) generically describes a marcfortine or paraherquamide derivative (i.e. partial formula (III) substituted at position 14 with methyl or methyl and hydroxy, however no description of how to prepare such 14-methyl-14-hydroxymarcfortine compounds is provided.

The *Journal of Antibiotics*, 43, 1380–1386 (1990) discloses Paraherquamide A which has the following structure:

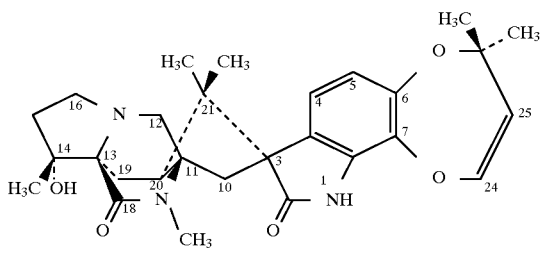

Marcfortine A has the following structure:

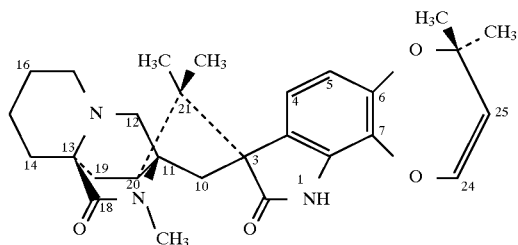

Marcfortine B has the following structure:

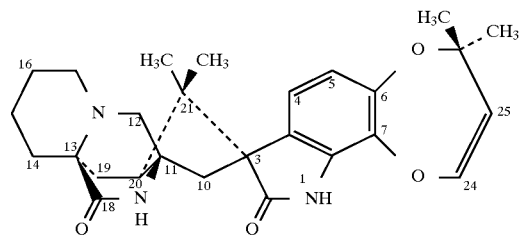

Marcfortine C has the following structure:

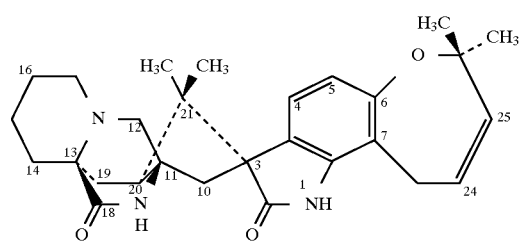

Marcfortine D has the following structure:

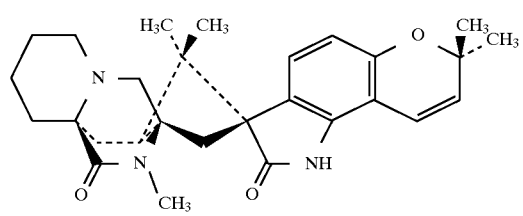

WO 91/09961 (published 11 Jul. 1991) discloses various derivatives of marcfortine and paraherquamide, and 12a-N-oxides thereof, as well as the production the production of VM 29919 (paraherquamide) and VM 55596 (the 12a-N-oxide of paraherquamide) inter alia from *Penicillium Sp.* IMI 332995.

U.S. Pat. No. 4,873,247 discloses derivatives of paraherquamide and a strain of *Penicillium charlessi* MF 5123 (ATCC 20841) for the production of paraherquamide. U.S. Pat. No. 4,978,656 (as well as EP 390532-A, EP-301742-A) discloses various synthetic derivatives of paraherquamide as well as the production of paraherquamide from *Penicillium charlessi* MF 5123 (ATCC 20841).

International Publication WO 92/22555 (published 23 Dec. 1992) generically discloses 14α-hydroxymarcfortine compounds and a process which uses the 14-hydroxy-14-methylmarcfortine compounds for the production of antiparasitic drugs. However, no enabling description of any means of preparation of 14α-hydroxymarcfortine or 14α-hydroxy-14β-methylmarcfortine compounds is provided.

International Publication WO94/29319 discloses various 14-substituted marcfortines and derivatives thereof.

The 15-alkyl-14-hydroxy compounds (III) where $n_1$ is 0 are known, see International Publication WO94/29319.

SUMMARY OF INVENTION

Disclosed are 25-methylene compounds of the formula (VII) where for:

(I) Marcfortine A
 (a) n is 1,
 (b) $R_{14}$ is $R_{14\alpha}{:}R_{14\beta}$ where $R_{14\alpha}$ is —H and $R_{14\beta}$ is —H,
 (c) $R_{15}$ is $R_{15\alpha}{:}R_{15\beta}$ where $R_{15\alpha}$ is —H and $R_{15\beta}$ is —H;

(II) Paraherquamide A
 (a) n is 0,
 (b) $R_{14}$ is $R_{14\alpha}{:}R_{14\beta}$ where $R_{14\alpha}$ is —OH and $R_{14\beta}$ is —CH$_3$,
 (c) $R_{15}$ is $R_{15\alpha}{:}R_{15\beta}$ where $R_{15\alpha}$ a is —H and $R_{15\beta}$ is —H;

(III) 14-hydroxy-14-alkyl Marcfortine A
 (a) n is 1,
 (b) $R_{14}$ is $R_{14\alpha}{:}R_{14\beta}$ where $R_{14\alpha}$ is —OH and $R_{14\beta}$ is $C_1$–$C_4$ alkyl,
 (c) $R_{15}$ is $R_{15\alpha}{:}R_{15\beta}$ where $R_{15\alpha}$ is —H and $R_{15\beta}$ is —H;

(IV) 14-hydroxy-15-methyl Marcfortine A
 (a) n is 1,
 (b) $R_{14}$ is $R_{14\alpha}{:}R_{14\beta}$ where $R_{14\alpha}$ is —OH and $R_{14\beta}$ is —H,
 (c) $R_{15}$ is $R_{15\alpha}{:}R_{15\beta}$ where $R_{15\alpha}$ is $C_1$–$C_4$ alkyl and $R_{15\beta}$ is —H and pharmaceutically acceptable salts thereof.

Also disclosed are 24,25-epoxy compounds of the formula (VIII) where for:

(I) Marcfortine A
 (a) n is 1,
 (b) $R_{14}$ is $R_{14\alpha}{:}R_{14\beta}$ where $R_{14\alpha}$ is —H and $R_{14\beta}$ is —H,
 (c) $R_{15}$ is $R_{15\alpha}{:}R_{15\beta}$ where $R_{15\alpha}$ is —H and $R_{15\beta}$ is —H;

(II) Paraherquamide A
 (a) n is 0,
 (b) $R_{14}$ is $R_{14\alpha}{:}R_{14\beta}$ where $R_{14\alpha}$ is —OH and $R_{14\beta}$ is —CH$_3$,
 (c) $R_{15}$ is $R_{15\alpha}{:}R_{15\beta}$ where $R_{15\alpha}$ is —H and $R_{15\beta}$ is —H;

(III) 14-hydroxy-14-alkyl Marcfortine A
 (a) n is 1,
 (b) $R_{14}$ is $R_{14\alpha}{:}R_{14\beta}$ where $R_{14\alpha}$ is —OH and $R_{14\beta}$ is $C_1$–$C_4$ alkyl,
 (c) $R_{15}$ is $R_{15\alpha}{:}R_{15\beta}$ where $R_{15\alpha}$ is —H and $R_{15\beta}$ is —H;

(IV) 14-hydroxy-15-methyl Marcfortine A
 (a) n is 1,
 (b) $R_{14}$ is $R_{14\alpha}{:}R_{14\beta}$ where $R_{14\alpha}$ is —H and $R_{14\beta}$ is —H,
 (c) $R_{15}$ is $R_{15\alpha}{:}R_{15\beta}$ where $R_{15\alpha}$ is $C_1$–$C_4$ alkyl and $R_{15\beta}$ is —H and pharmaceutically acceptable salts thereof.

Disclosed is N-(18a)-demethyl-2-deoxoparaherquamide A and pharmaceutically acceptable salts thereof.

DETAILED DESCRIPTION OF THE INVENTION

The present invention is 25-methylene (VII) and 24,25-epoxy (VIII) marcfortines and paraherquamides. These compounds are made by two different reactions from known compounds.

The 25-methylene marefortines and paraherquamides (VII) are produced from the known corresponding cyclic olefins (I). When (a) n is 1, (b) $R_{14}$ is $R_{14\alpha}{:}R_{14\beta}$ where $R_{14\alpha}$ is —H and $R_{14\beta}$ is —H and (c) $R_{15}$ is $R_{15\alpha}{:}R_{15\beta}$ where $R_{15\alpha}$ is —H and $R_{15\beta}$ is —H the starting cyclic olefin (I) is marcfortine A; when (a) n is 0, (b) $R_{14}$ is $R_{14\alpha}{:}R_{14\beta}$ where $R_{14\alpha}$ is —OH and $R_{14\beta}$ is —CH$_3$ and (c) $R_{15}$ is $R_{15\alpha}{:}R_{15\beta}$ where $R_{15\alpha}$ is —H and $R_{15\beta}$ is —H the starting cyclic olefin (I) is paraherquamide A; when (a) n is 1, (b) $R_{14}$ is $R_{14\alpha}{:}R_{14\beta}$ where $R_{14\alpha}$ is —OH and $R_{14\beta}$ is —CH$_3$ and (c) $R_{15}$ is $R_{15\alpha}{:}R_{15\beta}$ where $R_{15\alpha}$ is —H and $R_{15\beta}$ is —H the starting cyclic olefin (I) is 14-hydroxy-14-methyl marcfortine A and when (a) n is 1, (b) $R_{14}$ is $R_{14\alpha}{:}R_{14\beta}$ where $R_{14\alpha}$ is —OH and $R_{14\beta}$ is —H and (c) $R_{15}$ is $R_{15\alpha}{:}R_{15\beta}$ where $R_{15\alpha}$ is —CH$_3$ and $R_{15\beta}$ is —H the starting cyclic olefin (I) is 14-hydroxy-15-methyl marcfortine A Marcfortine A and paraherquamide A are well known compounds. The 14-Hydroxy-14-alkyl marcfortine A and 14-hydroxy-15-alkyl marcfortine A compounds are produced by the processes set forth in CHARTS C–H and PREPARATIONS 1–31. The CHARTS and PREPARATIONS exempilfy methyl as the alkyl substituent, however ethyl, propyl and butyl (including isomers thereof where such exist) are prepared in an analogous fashion as is known to those skilled in the art.

The 25-methylene compounds (VII) are produced from the corresponding cyclic olefin (I) first by cleavage of the seven member cyclic ether containing the olefin by use of a reagent such as formic acid to produce the diol (II). The diol (II) is then alkylated with an alkylating reagent to produce the corresponding olefin (III). The olefin (III) must have the double bond at the specified position to produce the desired product that when cyclized and oxidized will have a hydroxyl group at C-25. Such a reagent includes compounds of the formula, $X_1$—CH$_2$—CH=C(CH$_3$)$_2$ where $X_1$ is a leaving group such as —Br or —Cl; it is preferred that $X_1$ is —Br, it is more preferred that the reagent be 4-bromo-2-methyl-2-butene. This reaction is performed in the presence of potassium iodide and a weak base such as bicarbonate or carbonate (preferably potassium carbonate) in an aqueous-organic solvent mixture, preferably acetone/water. The olefin (III) is then oxidized to the corresponding epoxy-phenol (IV) by use of a peracid, preferably m-chloroperbenzoic acid followed by sodium bisulfite workup. The epoxy-phenol (IV) is then cyclized to the corresponding cyclic alcohol (V) by use of tin (IV) chloride. The cyclic alcohol (V) is then oxidized under Swern conditions (oxalyl chloride, DMSO followed by TEA) to give the corresponding ketone (VI). The ketone (VI) is then transformed to the desired 25-methylene compound (VII) by a Wittig reaction using methyltriphenylphosphonium bromide and a strong base such as n-butyl lithium. It is realized that the 25-methylene compound (VII) is a 24,25-dihydro compound.

The 24,25-epoxy compounds (VIII) are produced from the corresponding cyclic olefin (I) by oxidation with a peracid tnder normal conditions for peracid oxidation to epoxides followed by aqueous sodium bisulfite workup. It is preferred that the peracid be m-chloroperbenzoic acid.

N-(18a)-demethyl-2-deoxoparaherquamide A is also known as (1'α,5'aβ,7'β,8'aβ,9'aβ)-(-)-2,2',3,3',8a',9'-hexahydro-1'-hydroxy-1',4,4,8',8'-pentamethyl-spiro[4H,8H,-[1,4]dioxepino[2,3-g]indole-8,7'(8'H)-[5H,6H-5a,9a](iminomethano)[1H]cyclopent[f]indolizine]-9-one]. N-(18a)-demethyl-2-deoxoparaherquamide A can be prepared by two different methods, see EXAMPLEs 14 and 15.

The 25-methylene compounds (VII), 24,25-epoxy compounds (VIII) and N-(18a)-demethyl-2-deoxoparaherquamide A are amines, and as such form acid addition salts when reacted with acids of sufficient strength.

Pharmaceutically acceptable salts include salts of both inorganic and organic acids. The pharmaceutically acceptable salts are preferred over the corresponding free amines since they produce compounds which are more water soluble and more crystalline. The preferred pharmaceutically acceptable salts include salts of the following acids methanesulfonic, hydrochloric, hydrobromic, sulfuric, phosphoric, nitric, benzoic, citric, tartaric, fumaric, maleic, $CH_3—(CH_2)m—COOH$ where m is 0 thru 4, $HOOC—(CH_2)m—COOH$ where n is as defined above.

The 25-methylene compounds (VII), 24,25-epoxy compounds (VIII) and N-(18a)-demethyl-2-deoxoparaherquamide A of this invention are unexpectedly potent antiparasitic agents against endo and ecto parasites, particularly helminths and arthropods, which cause numerous parasitic diseases in humans, animals, and plants.

Parasitic diseases may be caused by either endoparasites or ectoparasites. Endoparasites are those parasites which live inside the body of the host, either within an organ (such as the stomach, lungs, heart, intestines, etc.) or simply under the skin. Ectoparasites are those parasites which live on the outer surface of the host but still draw nutrients from the host.

The endoparasitic diseases generally referred to as helminthiasis are due to infection of the host with parasitic worms known as helminths. Helminthiasis is a prevalent and serious worldwide economic problem due to infection of domesticated animals such as swine, sheep, horses, cattle, goats, dogs, cats, and poultry. Many of these infections are caused by the group of worms described as nematodes which cause diseases in various species of animals throughout the world. These diseases are frequently serious and can result in the death of the infected animal. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Many parasites are species specific (infect only one host) and most also have a preferred site of infection within the animal. Thus Haemonchus and Ostertagia primarily infect the stomach while Nenmatodirus and Cooperia mostly attack the intestines. Other parasites prefer to reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Infections by ectoparasitic arthropods such as ticks, mites, lice, stable flies, hornflies, blowflies, fleas, and the like are also a serious problem. Infection by these parasites results in loss of blood, skin lesions, and can interfere with normal eating habits thus causing weight loss. These infections can also result in transmission of serious diseases such as encephalitis, anaplasmosis, swine pox, and the like which can be fatal.

Animals may be infected by several species of parasite at the same time since infection by one parasite may weaken the animal and make it more susceptible to infection by a second species of parasite. Thus a compound with a broad spectrum of activity is particularly advantageous in the treatment of these diseases. The 25-methylene compounds (VII), 24,25-epoxy compounds (VIII) and N-(18a)-demethyl-2-deoxoparaherquamide A have unexpectedly high activity against these parasites, and in addition, are also active against Dirofilaria in dogs, Nematospiroides and Syphacia in rodents, biting insects and migrating dipterous larvae such as Hypoderma sp. in cattle, and Gastrophilus in horses.

The 25-methylene compounds (VII), 24,25-epoxy compounds (VII) and N-(18a)-demethyl-2-deoxoparaherquamide A are also useful against endo and ecto parasites which cause parasitic diseases in humans. Examples of such endoparasites which infect man include gastro intestinal parasites of the genera Ancylostoma, Necator, Ascaris, Strongyloides, Trichinella, Capillaria, Trichuris, Enterobius, and the like. Other endoparasites which infect man are found in the blood or in other organs. Examples of such parasites are the filarial worms Wucheria, Brugia, Onchocerca, and the like as well as extra intestinal stages of the intestinal worms Strongylides and Trichinella. Ectoparasites which parasitize man include arthropods such as ticks, fleas, mites, lice, and the like and, as with domestic animals, infections by these parasites can result in transmission of serious and even fatal diseases. The 25-methylene compounds (VII), 24,25-epoxy compounds (VIII) and N-(18a)-demethyl-2-deoxoparaherquamide A are active against these endo and ecto parasites and in addition are also active against biting insects and other dipterous pests which annoy humans. The 25-methylene compounds (VII), 24,25-epoxy compounds (VIII and N-(18a)-demethyl-2-deoxoparaherquamide A when administered orally or parenterally are administered at a dosage rate of from 0.05 to 20 mg/kg of animal body weight.

The 25-methylene compounds (VII), 24,25-epoxy compounds (VIII) and N-(18a)-demethyl-2-deoxoparaherquamide A are also useful against common household pests such as Blatella sp. (cockroach), Tineola sp. (clothes moth), Attagenus sp. (carpet beetle), Musca domestica (housefly) and against Solenopsis Invicta (imported fire ant).

The 25-methylene compounds (VII), 24,25-epoxy compounds (VIII) and N-(18a)-demethyl-2-deoxoparaherquamnide A are furthermore useful against agricultural pests such as aphids (Acyrthiosiphon sp.), locusts, and boll weevils as well as against insect pests which attack stored grains such as Tribolium sp. and against immature stages of insects living on plant tissue. The 25-methylene compounds (VII), 24,25-epoxy compounds (VIII) and N-(18a)-demethyl-2-deoxoparaherquamide A are also useful as a nematocide for the control of soil nematodes which may be agriculturally important.

For use as an antiparasitic agent in animals the 25-methylene compounds (VII), 24,25-epoxy compounds (VIII) and N-(18a)-demethyl-2-deoxoparaherquamide A may be administered internally either orally or by injection, or topically as a liquid drench or as a shampoo.

For oral administration, the 25-methylene compounds (VI), 24,25-epoxy compounds (VIII) and N-(18a)-demethyl-2-deoxoparaherquamide A may be administered in capsule, tablet, or drench bolus form or alternatively they can be mixed in the animals feed. The capsules, tablets, and drenches boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, suspending agents, and/or binders such that a uniform mixture solution or suspension is obtained. An inert ingredient is one that will not react with the 25-methylene compounds (VI), 24,25-epoxy compounds (VIII) and N-(18a)-demethyl-2-deoxoparaherquarnide A and which is non toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the 25-methylene compounds (VII), 24,25-epoxy compounds (VIII) and N-(1 8a)-demethyl-2-deoxoparaherquamide A with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5.0% by weight of the active ingredient.

The 25-methylene compounds (VII), 24,25-epoxy compounds (VIII) and N-(18a)-demethyl-2-deoxoparaherquamide A may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 20% by weight of the active ingredient.

Topical application of the 25-methylene compounds (VII), 24,25-epoxy compounds (VIII) and N-(1a)-demethyl-2-deoxoparaherquamide A is possible through the use of a liquid drench or a shampoo containing the 25-methylene compounds (VII), 24,25-epoxy compounds (VIII) and N-(18a)-demethyl-2-deoxoparaherquamide A as an aqueous solution or suspension. These formulations generally contain a suspending agent such as bentonite and normally will also contain an antifoaming agent. Formulations containing from 0.005 to 20% by weight of the active ingredient are acceptable. Preferred formulations are those containing from 0.5 to 5% by weight of the 25-methylene compounds (VII), 24,25-epoxy compounds (VIII) and N-(18a)-demethyl-2-deoxoparaherquamide A.

The 25-methylene compounds (VII), 24,25-epoxy compounds (VIII) and N-(18a)-demethyl-2-deoxoparaherquamide A are primarily useful as antiparasitic agents for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans. In treating such infections the 25-methylene compounds (VII), 24,25-epoxy compounds (VIII) and N-(18a)-demethyl-2-deoxoparaherquamide A may be used individually or in combination with each other or with other unrelated antiparasitic agents. The dosage of the 25-methylene compounds (VII), 24,25-epoxy compounds (VII) and N-(1 8a)-demethyl-2-deoxoparaherquamide A required for best results depends on several factors such as the species and size of the animal, the type and severity of the infection, the method of administration and the particular 25-methylene compounds VII), 24,25-epoxy compounds (VIII) and N-(18a)-demethyl-2-deoxoparaherquamide A used. Oral administration of the 25-methylene compounds (VII), 24,25-epoxy compounds (VIII) and N-(18a)-demethyl-2-deoxopamherquamide A at dose level of from 0.005 to 50 mg per kg of animal body weight either in a single dose or in several doses spaced a few days apart, generally gives good results. A single dose of one of the 25-methylene compounds (VII), 24,25-epoxy compounds (VIII) and N-(18a)-demethyl-2-deoxoparaherquamide A normally gives excellent control however repeat doses may be given to combat re-infection or for parasite species which are unusually persistent. The techniques for administering the 25-methylene compounds (VII), 24,25-epoxy compounds (VIII) and N-(18a)-demethyl-2-deoxoparaherquamide A to animals are known to those skilled in the veterinary field.

The 25-methylene compounds (VII), 24,25-epoxy compounds (VII) and N-(18a)-demethyl-2-deoxoparaherquamide A may also be used to combat agricultural pests which attack crops either in the field or in storage. The 25-methylene compounds (VII), 24,25-epoxy compounds (VIII) and N-(18a)-demethyl-2-deoxoparaherquamide A are applied for such uses as sprays, dusts, emulsions and the like either to the growing plants or the harvested crops. The techniques for applying the 25-methylene compounds (VII), 24,25-epoxy compounds (VIII) and N-(18a)-demethyl-2-deoxoparaherquamide A in this manner are known to those skilled in the agricultural arts.

The exact dosage and frequency of administration depends on the particular 25-methylene compounds (VII), 24,25-epoxy compounds (VIII) and N-(18a)-demethyl-2-deoxoparaherquamide A used, the particular condition being treated, the severity of the condition being treated, the age, weight, general physical condition of the particular patient, other medication the individual may be taking as is well known to those skilled in the art and can be more accurately determined by measuring the blood level or concentration of the 25-methylene compounds (VII), 24,25-epoxy compounds (VIII) and N-(1 8a)-demethyl-2-deoxoparaherquamide A in the patient's blood and/or the patient's response to the particular condition being treated.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—$C(Z=Z_1)$ H. Groups $R_i$ and $R_j$ would represent monovalent variable substituents if attached to the formula $CH_3$—$CH_2$—$C(R_i)$ ($R_j$)—H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—$CH(R_i)$—$CH_3$ represents a 2-substituted-1-methoxypropane compound. In a similar fashion, the symbol "=" represents a double bond, e.g., $CH_2$=$C(R_i)$—O—$CH_3$, and the symbol "≡" represents a triple bond, e.g., HC≡C-$CH(R_i)$—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4chloro-2-methylpyridine can be represented in linear fashion by N*=$C(CH_3)$—CH=CCl—CH=C*H with the convention that the atoms marked with an asterisk (*) are bonded to each other resulting in the formation of a ring. Likewise, the cyclic molecular fragment, 4(ethyl)-1-piperazinyl can be represented by —N*—$(CH_2)_2$—N$(C_2H_5)$—$CH_2$—C*$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —$C(X_1)(X_2)$— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha (α) configuration and is identified by a broken, dashed or dotted line attachment to the carbon atom, i.e., by the symbol "- - -" or ". . .". The corresponding substituent attached "above" ($X_2$) the other ($X_1$) is identified as being in the beta (β) configuration and is indicated by an unbroken line attachment to the carbon atom.

When a variable substituent is bivalent, the valences may be taken together or separately or both in the definition of the variable. For example, a variable $R_i$ attached to a carbon atom as —$C(=R_i)$— might be bivalent and be defmed as oxo or keto (thus forming a carbonyl group (—CO—) or as two separately attached monovalent variable substituents α-$R_{i\text{-}j}$ and β$R_{i\text{-}k}$. When a bivalent variable, $R_i$, is defined to consist of two monovalent variable substituents, the convention used to define the bivalent variable is of the form "α-$R_{i\text{-}j}$:β-$R_{i\text{-}k}$" or some variant thereof. In such a case both α-$R_{i\text{-}j}$ and β-$R_{i\text{-}k}$ are attached to the carbon atom to give —C(α-$R_{i\text{-}j}$)(β-$R_{i\text{-}k}$)—. For example, when the bivalent variable $R_6$, —C(=$R_6$)— is defined to consist of two monovalent variable substituents, the two monovalent variable substituents are α-$R_{6\text{-}1}$:β-$R_{6\text{-}2}$, . . . α-$R_{6\text{-}9}$:β-$R_{6\text{-}10}$, etc, giving —C(α-$R_{6\text{-}1}$)(β-$R_{6\text{-}2}$)—, . . . —C(α-$R_{6\text{-}9}$)(β-$R_{6\text{-}10}$)—, etc. Likewise, for the bivalent variable $R_{11}$, —C(=$R_{11}$)—, two monovalent variable substituents are α-$R_{11\text{-}1}$:β-$R_{11\text{-}2}$. For a ring substituent for which separate α and β orientations do not exist (e.g. due to the presence of a carbon carbon double bond in the ring), and for a substituent bonded to a carbon atom which is not part of a ring the above convention is still used, but the a and β designations are omitted.

Just as a bivalent variable may be defined as two separate monovalent variable substituents, two separate monovalent variable substituents may be defined to be taken together to form a bivalent variable. For example, in the formula —$C_1$,($R_i$)H—$C_2$($R_j$)H—($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation ". . . $R_i$ and $R_j$ are taken together to form —$CH_2$—$CH_2$—O—CO— . . ." means a lactone in which the carbonyl is bonded to $C_2$. However, when designated ". . . $R_j$ and $R_i$ are taken together to form —CO—O—$CH_2$—$CH_2$-the convention means a lactone in which the carbonyl is bonded to $C_1$.

The carbon atom content of variable substituents is indicated in one of two ways. The first method uses a prefix to the entire name of the variable such as "$C_1$–$C_4$", where both "1" and "4" are integers representing the mini mum and maximum number of carbon atoms in the variable. The prefix is separated from the variable by a space. For example, "$C_1$–$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$–$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$–$C_j$" designation in parentheses and placing it immediately (no intervening space) before the portion of the definition being defined. By this optional convention ($C_1$–$C_3$)alkoxycarbonyl has the same meaning as $C_2$–$C_4$ alkoxycarbonyl because the "$C_1$–$C_3$" it refers only to the carbon atom content of the alkoxy group. Similarly while both $C_2$–$C_6$ alkoxyalkyl and ($C_1$–$C_3$)alkoxy($C_1$–$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

All temperatures are in degrees Centigrade.

THF refers to tetrahydrofuran.

DMSO refers to dimethylsulfoxide.

LDA refers to lithium diisopropylamide.

TEA refers to triethylamine.

DMF refers to dimethylformamide.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

NMR refers to nuclear (proton) magnetic resonance spectroscopy, chemical shifts are reported in ppm ($\delta$) downfield from tetramethylsilane.

—$\phi$ refers to phenyl ($C_6H_5$).

MS refers to mass spectrometry expressed as m/e, m/z or mass/charge unit. $[M+H]^+$ refers to the positive ion of a parent plus a hydrogen atom. EI refers to electron impact. CI refers to chemical ionization. FAB refers to fast atom bombardment.

HRMS refers to high resolution mass spectrometry.

Ether refers to diethyl ether.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

_ indicates that there are 2 possible orientations for the attached group, (1) $\alpha$ or $\beta$ when attached to the steroid ring and (2) cis or trans when attached to a carbon atom of a double bond.

UC#### refers to the Upjohn Culture number abcd.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

16-Iodo-17-cyanomarcfortine A as a mixture of diastereomers (Formula 5)

Solid cyanogen iodide (11.7 g, 76.5 mmol) is added to a solution of marcfortine A (10.5 g, 22 mmol) in chloroform (150 mL) and the reaction mixture heated under reflux until all of the marcfortine A has been consumed (about 5 hr). The resulting mixture is cooled to 20°–25°, diluted with methylene chloride (100 mL), washed with sat sodium bicarbonate and then washed with a solution of sodium sulfite. The organic phase is separated, dried over magnesium sulfate and concentrated to dryness. The resulting crude solid is subjected to chromatography (silica gel; ethyl acetate/hexane, 3/2) to give the title compound.

PREPARATION 2

16,17-Dehydro-17-cyanomarcfortine A (Formula 6)

16-Iodo-17-cyanomarcfortine A (PREPARATION 1, 9.5 g, 15 mmol) is dissolved in methanol (150 mL), and aqueous potassium hydroxide (45%, 3 mL) is added. The reaction mixture is stirred at 20°–25° for 2 hr. Water is added and the resulting precipitate collected by filtration, washed with water and dried overnight under reduced pressure to give the title compoound.

PREPARATION 3

17-Ketomarcfortine A (Formula 7)

Selenium dioxide (2.9 g, 26 mmol) is added to a solution of 16,17-dehydro-17-cyanomarcfortine A (PREPARATION 2, 6.0 g, 10 mmol) in 95% ethanol (100 mL) and the reaction mixture stirred at 20°–25° for 2 hr. The reaction is quenched by adding saturated sodium bicarbonate (100 mL). The resulting mixture is extracted with methylene chloride (2×200 mL). The extracts are combined, dried (magnesium sulfate), and concentrated to give crude product. This material is purified by chromatography (silica gel; ethyl acetate) to give the title compound, HRMS (FAB, M/Z, [M+H]) calculated for $C_{28}H_{33}N_3O_5+H=492.2498$, measured=492.2478.

Alternatively, and more preferably, the title compound can be synthesized by using p-toluenesufonic acid. Thus, p-toluenesulfonic acid monohydrate (1 g) is added to a solution of 16,17-dehydro-17-cyanomarcfortine A (10 g) in 95% methanol (50 mL) and the reaction mixture stirred at 20°–25° for 1 hr. Triethylamine (2 mL) is added to the mixture and the solvent is evaporated. The residue is triturated with aqueous sodium carbonate solution (10%, 100 mL) and the solid is filter and dried to give the title compound as a solid (90% yield).

PREPARATION 4

15,16-Dehydro-17-ketomarcfortine A (Formula 8)

A solution of lithium diisopropylamide is prepared from a solution of n-butyl lithium (1.6M, 9.9 mL, 15.4 mmol) in hexane and diisopropylamine (2.2 mL, 15.7 mmol). This is diluted with anhydrous tetaahydrofuran (THF, 20 mL) and cooled to at −78°. A solution of 17-ketomarcfortine A (PREPARATION 3, 2.0 g, 4.1 mmol) in anhydrous THF (20 mL) is added dropwise and the reaction mixture allowed to warm to −40° during 1 hr. The mixture is again cooled to −78° and treated dropwise with phenyl selenium chloride (19 mg, 5.2 mmol) in THF (10 mL). After 5 min the reaction is quenched with saturated sodium bicarbonate, extracted with methylene chloride, dried (magnesium sulfate), and concentrated to give a solid which is used without further purification. This material is dissolved in THF (150 mL) and treated with hydrogen peroxide (30%, 1.5 mL) at 0°. The cooling bath is removed and the reaction mixture stirred for 30 min at 20°–25°. The reaction is quenched by adding sodium hydroxide (1N, 100 mL). The mixture is extracted with methylene chloride (2×200 mL). The extracts are combined, dried (magnesium sulfate) and concentrated to give crude product. This material is purified by chromatography (silica gel; ethyl acetate) to give the title compound, HRMS (FAB, M/Z, [M+H]) calculated for $C_{28}H_{31}N_3O_5+H=490.2342$, measured=490.2345.

PREPARATION 5

14$\alpha$-Hydroxy-15,16-dehydro-17-ketomarcfortine A (Formula 9a) Using Oxaziridine Chemistry A solution of potassium bis(trimethylsilyl)amide in toluene (0.5M, 1 mL, 0.5 mmol) is added dropwise to a solution of 15,16-dehydro-17-ketomarcfortine A (PREPARATION 4, 66 mg, 0.14 mmol) in THF (2 mL) at −78°. The resulting mixture is allowed to warm to −40° during 1 hr. The reaction mixture is cooled to −78°, stirred 15 min and then treated by the dropwise addition of a solution of 2-phenylsulfonyl-3-phenyloxaziridine (42 mg, 0.16 mmol) in THF (2 mL). The mixture is stirred 5 min after which the reaction is quenched by adding sodium bicarbonate. The mixture is extracted with methylene chloride (2×25 mL). The extracts are combined, dried (magnesium sulfate) and concentrated to give crude material. This is purified by preparative thin layer chromatography (silica gel; ethyl acetate) to give the title compound, HRMS (FAB, M/Z [M+H]) calculated for $C_{28}H_{31}N_3O_6$+H=506.2291, measured=506.2280.

14,15-Debydro-16-hydroxy-17-ketomarcfortine A (14 mg, 20%) is also obtained.

PREPARATION 6
14α-Hydroxy-15,16-dehydro-17-ketomarcfortine A (Formula 9a), 15,16-dehydro-14,17-diketomarcfortine A (Formula 11) and 14,15-dehydro-16,17-diketomarcfortine A (Formula 24) Using Selenium Dioxide 15,16-Dehydro-17-ketomarcfortine A (PREPARATION 4, 1.29 g, 2.6 mmol) is dissolved in p-dioxane (30 mL) and treated with selenium dioxide (390 mg). The mixture is refluxed for 1 hr and the solvent evaporated under reduced pressure. The residue is triturated with methylene chloride (30 mL) and filtered. The filtrate is concentrated and the residue subjected to chromatography (silica gel; methanol/ethyl acetate, 1/20) to give 14α-hydroxy-15,16-dehydro-17-ketomarcfortine A (430 mg, 32%) as a solid. 15,16-Dehydro-14,17-diketomarcfortine A (Formula 11, 212 mg, 16%) and 14,15-dehydro-16,17-diketomarcfortine A (Formula 24, 106 mg, 8%) are also obtained from the chromatography.

PREPARATION 7
15,16-dehydro-14,17-diketomarcfortine A (Formula 11)

14α-Hydroxy-15,16-dehydro-17-ketomarcfortine A (PREPARATION 6, 60 mg, Formula 9a) is dissolved in methylene chloride (10 mL) and treated with manganese dioxide (60 mg). The mixture is stirred at 20°–25° for 1 hr and concentrated. Preparative thin layer chromatography of the residue (silica gel; methylene chloride/ethyl acetate, 50/50) gives the title compound.

PREPARATION 8
14α-hydroxymarcfortine A (Formula 10)

14α-Hydroxy-15,16-dehydro-17-ketomarcfortine A (PREPARATION 6, 20 mg, 0.040 mmol) is dissolved in THF (5 mL) and treated with a solution of lithium aluminum hydride (1M, 0.11 mL, 0.11 mmol) in THF at 0°. The mixture is stirred for 0.5 hr at 0° after which a solution of sodium bicarbonate (10%) is added. The mixture is extracted with methylene chloride (2×10 mL). The extracts are combined, dried (magnesium sulfate) and the solvent removed under reduced pressure. Preparative thin layer chromatography (silica gel; methanol/ethyl acetate, 10/90) gives the title compound, HRMS (FAB, M/Z, [M+H]) calculated for $C_{28}H_{35}N_3O_5$+H=494.2655, measured=494.2653.

PREPARATION 9
14α-Hydroxy-17-ketomarcfortine A (Formula 12a)

14α-Hydroxy-15,16-dehydro-17-ketomarcfortine A (formula 9a, PREPARATION 6, 50 mg, 0.1 mnmol) is dissolved in THF (5 mL) and treated with a solution of lithium triethylborohydride in THF (1M, 0.7 mL) at −78°. The mixture is stirred for 0.5 hr at −78°. The reaction is quenched by adding methanol (1 mL) and the mixture is concentrated. The resulting solid is subjected to chromatography (silica gel; methanol/methylene chloride, 1/20) to give the title compound, HRMS (FAB, M/Z, [M+H]) calculated for $C_{28}H_{33}N_3O_6$+H=508.2447, measured=508.2437.

PREPARATION 10
Preparation of 14α-hydroxy-17-ketomarcfortine A (Formula 12a) and 14β-hydroxy-17-ketomarcfortine A from 15,16-dehydro-14,17-diketomarcfortine A (Formula 11)

15,16-Dehydro-14,17-diketomarcfortine A (Formula 11, PREPARATION 6, 470 mg, 0.93 mmol) is dissolved in THF and treated with a solution of lithium borohydride in THF (1M, 2 mL) at 20°–25°. The mixture is stirred for 2 hr after which a solution of sodium bicarbonate (10%) is added. The mixture is extracted with methylene chloride (2×20 mL). The extracts are combined, dried (magnesium sulfate) and the solvent evaporated. The residue contains a mixture of the two epimers which are readily separated by chromatography (silica gel; methanol/ethyl acetate, 1/20)-14α-hydroxy-17-ketomarcfortine A (90 mg, 19%) and 14β-hydroxy-17-ketomarcfortine A (94 mg, 20%).

PREPARATION 11
Preparation of 14α-hydroxymarcfortine A (Fonnula 10) from 14α-hydroxy-17-ketomarcfortine A (Formula 12a)

14α-Hydroxy-17-ketomarcfortine A (Formula 12a, PREPARATION 10, 413 mg, 0.81 mmol) is dissolved in THF (20 mL) and treated with a solution of borane THF complex in THF (1M, 2.43 mL) at 0°. The mixture is stirred for 2.25 hr. The mixture is stirred for 0.5 hr after which methanol (3 mL) is added. After the solvent is evaporated, the residue is subjected to chromatography (silica gel; methanol/ethyl acetate, 1/16) to give the title compound.

PREAPARATION 12
14,17-Diketomarcfortine A (Formula 13)

A solution of oxalyl chloride (40 μL) in anhydrous methylene chloride (5 mL) is treated with dimethyl sulfoxide (45 μL) at −78°. The mixture is stirred for 1 hr at −78°. A solution of 14α-hydroxy-17-ketomarcfortine A (PREPARATION 11, 27 mg) in methylene chloride (2 mL) is added dropwise. The reaction mixture is stirred 20 min at −78°. Triethylamine (0.3 mL) is added to the reaction mixture which is allowed to warm to 20°–25° during 20 min. The mixture is partitioned between sodium carbonate (10%, 10 mL) and methylene chloride (10 mL). The organic layer is separated, dried (magnesium sulfate) and concentrated. The residue is subjected to chromatography (silica gel; methanol/methylene chloride, 1/20) to give the title compound, HRMS (FAB, M/Z, [M+H]) calculated for $C_{28}H_{31}N_3O_6$+H=506.2291, measured=506.2280.

PREPARATION 13
14α-Hydroxy-14β-methyl-17-ketomarcfortine A (Formula 14a)

A solution of 14,17-Diketomarcfortine A (PREPARATION 12, 16 mg, 0.032 mmol) in methylene chloride (5 mL) at −78° is treated with a solution of methylmagnesium bromide (3M, 0.16 mL, 0.48 mmol) in ether at −78°. The resulting mixture is stirred for 0.5 hr at −78°. The reaction is quenched by adding sodium carbonate (10%, a few drops). The mixture is diluted with methylene chloride (10 mL), dried (magnesium sulfate) and concentrated. The residue is subjected to chromatography (silica gel; methanol/methylene chloride, 1/20) to give 14α-hydroxy-14β-methyl-17-ketomarcfortine A (8 mg, 50%, $R_f$=0.25), HRMS (FAB, M/Z, [M+H]) calculated for $C_{29}H_{35}N_3O_6$+H=522.2604, measured=522.2620.

Also obtained from the layer is 14β-hydroxy-14α-methyl-17-ketomarcfortine A (1.2 mg, 7%, $R_f$=0.4), HRMS (FAB, M/Z, [M+H]) calculated for $C_{29}H_{35}N_3O_6$+H=522.2604, measured=522.2630. The 6:1 ratio of products thus obtained is increased to greater than 50:1 and the yield increased to 80% when THF is used as the reaction solvent in place of methylene chloride.

PREPARATION 14

14α-hydroxy-14β-methylmarcfortine A (Formula 15)

A solution of 14α-hydroxy-14β-methyl-17-ketomarcfortine A (PREPARATION 13, 5 mg, 0.01 mmol) in THF (5 mL) is treated with a solution of lithium aluminum hydride (1M, 0.03 mL, 0.03 mmol) in THF at 0°. The mixture is stirred for 0.5 hr at 0° after which a solution of sodium bicarbonate (10%) is added. The mixture is extracted with methylene chloride (2×5 mL). The extracts are combined, dried (magnesium sulfate) and the solvent evaporated. Preparative TLC (silica gel; ethanol/methylene chloride, 1/20) gives the title compound, HRMS (FAB, M/Z, [M+H]) calculated for $C_{29}H_{37}N_3O_5$+H=508.2811, measured=508.2816.

PREPARATION 15

14-Ketomarcfortine A (Formula 16)

A solution of oxalyl chloride (150 μL) in anhydrous methylene chloride (20 mL) is treated with DMSO (170 μL) at −78°. The mixture is stirred for 1 hr at −78°. A solution of 14α-hydroxymarcfortine A (PREPARATION 11, 110 mg) in methylene chloride (5 mL) is added dropwise. The reaction mixture is stirred 20 min at −78°. TEA (1 mL) is added to the reaction mixture which is allowed to warm to 20°–25° during 20 min. The mixture is partitioned between sodium carbonate (10%, 20 mL) and methylene chloride (20 mL). The organic layer is separated, dried (magnesium sulfate) and concentrated. The residue is subjected to chromatography (silica gel; methanol/methylene chloride, 1/25) to give the title compound, HRMS (FAB, M/Z, [M+H]) calculated for $C_{28}H_{33}N_3O_5$+H=492.2498, measured=492.2510.

PREPARATION 16

14β-Hydroxymarcfortine A (Formula 17)

A solution of 14-ketomarcfortine A (PREPARATION 15, 10 mg) in methanol (2 mL) is treated with sodium borohydride (5 mg) at 0°. The mixture is stirred for 0.5 hr at 0° after which a solution of sodium bicarbonate (10%) is added. The mixture is extracted with methylene chloride (2×10 mL). The extracts are combined, dried (magnesium sulfate) and the solvent evaporated. Preparative TLC (silica gel, methanol/ethyl acetate, 1/16) gives the title compound, HRMS (FAB, M/Z, [M+H]) calculated for $C_{28}H_{35}N_3O_5$+H=494.2655, measured=494.2653.

PREPARATION 17

14α-Hydroxymarcfortine A N-oxide (Formula 18)

A solution of 14α-hydroxymarcfortine A (PREPARATION 11, 15 mg) in methylene chloride (3 mL) is treated with m-chloroperoxybenzoic acid (15 mg) at 0°. After the mixture is stirred for 0.5 hr at 0°, treated with TEA (30 μL) and concentrated. Preparative TLC (silica gel; methanol/methylene chloride, 1/8) give the title compound, HRMS (FAB, M/Z, [M+H]) calculated for $C_{28}H_{35}N_3O_6$+H=510.2604, measured=510.2615.

PREPARATION 18

14α-Hydroxy-14β-ethylmarcfortine A (Formula 19)

A solution of 14-ketomarcfortine A (PREPARATION 15, 25 mg, 0.05 mmol) in THF (5 mL) at −78° is treated with a solution of ethylmagnesium bromide (3M, 0.15 mL, 0.45 mmol) in ether at −78°. The resulting mixture is stirred for 0.5 hr at −780. The reaction mixture is allowed to warm to 20°–25° during 20 min. The reaction is quenched by adding sodium carbonate (10%, a few drops). The mixture is diluted with methylene chloride (10 mL), dried (magnesium sulfate) and concentrated. The residue is subjected to chromatography (silica gel; methanol/methylene chloride, 1/20) to give the title compound, HRMS (FAB, M/Z, [M+H]) calculated for $C_{30}H_{39}N_3O_5$+H=522.2968, measured=522.2983.

PREPARATION 19

Preparation of 14β-methylmarcfortine A from 14α-hydroxy-14β-methylmarcfortine A

A solution of potassium bis(trimethylsilyl)amide in toluene (0.5M, 1 mL, 0.5 mmol) is added dropwise to a solution of 14α-hydroxy-14β-methylmarcfortine A (Formula 15, PREPARATION 14, 66 mg, 0.14 mmol) in THF (2 mL) at −78°. The resulting mixture is allowed to warm to −40° during 1 hr. The reaction mixture is cooled −78°, stirred 15 min, and then treated by the dropwise addition of a solution of phenylchlorothionoformate (0.094 mL, 0.7 mmol) in THF (2 mL). After 10 min the dry ice bath is removed. After frrther reaction for 3 hr, the reaction is quenched by adding sodium bicarbonate. The mixture is extracted with methylene chloride (2×25 mL). The extracts are combined, dried (magnesium sulfate) and concentrated to give crude material. This is purified by preparative TLC (silica gel, ethyl acetate) to give 14α-O-phenoxythiocarbonyl-14β-methylmarcfortine A.

To a solution of 14α-O-phenoxythiocarbonyl-14β-methylmarcfortine A (64 mg, 0.1 mmol) in toluene (5 mL) is added AIBN (2,2'-azabisisobutyonitrile, 3.3 mg) followed by addition of tributyltin hydride (54 μL, 0.2 mmol). The mixture is refluxed for 3 hr. After the solvent is evaporated, the residue is purified by preparative TLC (silica gel, ethyl acetate) to give 14β-methylmarcfortine A.

PREPARATION 20

An Alternative Synthesis Of 17-ketomarcfortine A (Formula 7)

To marcfortine A (65 g, 0.136 mol) and sodium bicarbonate (137 g, 1.63 mol) in tetrahydrofuran (THF, 2 L) and water (1.25 L) at reflux is added iodine (206 g, 0.81 mol) dropwise in THF (1.25 L) over a one hour period. (Alternatively, the mixture can be stirred at 20°–25° for 16 hours). After being allowed to slowly cool to 20°–25° (2.5 hr), the reaction is quenched with saturated sodium thiosulfate (1.5 L) and extracted with ethyl acetate (2×1 L). The combined organic layers are washed with saturated sodium thiosulfate (1 L), dried (magnesium sulfate), filtered, evaporated and dried overnight in the vacuum oven (65°) to give 62 g of crude 17-ketomarcfortine A (Formula 7), NMR (300 MHz, $CDCl_3$) 7.68, 6.80, 6.70, 6.32, 4.90, 3.75, 3.23, 3.09, 2.80, 2.65, 2.49–2.21, 2.08, 1.98–1.45, 1.46, 1.44, 1.09 and 0.90 δ.

Alternatively, iodine monochloride (ICl) can be used instead of iodine.

PREPARATION 21

16-Dithiophenyl-17-ketomarcfortine A (Formula 20)

The crude 17-ketomarcfortine A (PREPARATION 20, 5 g, 10.2 mmol) is added via a cannula in THF (150 mL) at −78° to an LDA solution which was prepared by adding n-butyllithium (1.6M, 24.8 mL, 0.04 mol) dropwise to diisopropyl amine (5.7 mL, 0.041 mol) at 0° in THF (100 mL). The reaction mixture is allowed to slowly warm to −50° over one hr. The resulting mixture is then treated with phenyl disulfide (4.4 g, 0.02 mol). The reaction is immediately quenched with saturated sodium bicarbonate solution (100 niL) and extracted with methylene chloride (300 niL). The organic phase is dried (magnesium sulfate), concentrated (8 g) and chromatographed (silica gel, 120 g; ethyl acetatelhexane, 60/40) to give the the title compound, MS (FAB)=708 (M$^+$+H); NMR (300 MHz, CDCl$_3$) 7.74, 7.71, 7.64, 7.45–7.30, 6.81, 6.72, 6.32, 4.91, 3.70, 3.16, 3.01, 2.75, 2.53, 2.35, 2.15–1.50, 1.47, 1.45, 1.06 and 0.82 δ.

PREPARATION 22
16-Thiophenyl-16-sulfoxyphenyl-17-ketomarcfortine A (Formula 21)

To 16-dithiophenyl-17-ketomarcfortine A (PREPARATION 21, 10 g, 14 mmol) in methylene chloride (250 mL) at −78° under a nitrogen atmosphere is added m-chloroperoxybenzoic acid (64%, 4.2 g, 15.5 mmol) dropwise in methylene chloride (200 mL) for 15 min. The reaction is immediately quenched with saturated sodium thiosulfate (200 mL), diluted with saturated sodium bicarbonate (200 mL) and extracted into methylene chloride (200 mL). Drying (magnesium sulfate), followed by concentration under reduced pressure gives the title compound NMR (300 MHz, CDCl$_3$) 8.0–7.29, 6.80, 6.70, 6.31, 4.90, 3.68, 3.41, 3.14, 3.07, 2.82, 2.80–2.65, 2.16, 2.05–1.1, 1.47, 1.43, 0.96 and 0.83 δ.

PREPARATION 23
16-Thiophenyl-15,16-dehydro-17-ketomarcfortine A (Formula 22)

The crude 16-thiophenyl-16-sulfoxyphenyl-17-ketomarcfortine A (Formula 21, PREPARATION 22, 11 g) is refluxed in toluene (250 mL) for 45 minutes, cooled to 20°–25°, diluted with saturated sodium bicarbonate (300 mL) and extracted with ethyl acetate (300 mL). The organic layer is dried (magnesium sulfate) and concentrated to give the title compound, MS (FAB)=598(M$^+$+H); HRMS (M/Z, M$^+$+H) C$_{34}$H$_{35}$N$_3$O$_5$S+H$_1$, calculate=598.2376, observed=598.2387; NMR (300 MHz, CDCl$_3$) 8.18, 7.55–7.45, 7.29–7.45, 6.83, 6.70, 6.34, 5.92, 4.91, 3.87, 3.30, 3.21, 3.08, 2.80, 2.35, 2.10, 2.03, 1.78, 1.46, 1.44, 1.11 and 0.88 δ.

PREPARATION 24
16-Sulfoxyphenyl-15,16-dehydro-17-ketomarcfortine A (Formula 23)

To the crude 16-thiophenyl-15,16-dehydro-17-ketomarfortine A (Formula 22, PREPARATION 23, 10.6 g) in methylene chloride (300 mnL) at −78° is added m-chloroperbenzoic acid (64%, 2.8 g) dropwise in methylene chloride (125 mL). The reaction is quenched with saturated sodium thiosulfate (300 mL) and saturated sodium bicarbonate (300 mL), then extracted into methylene chloride (300 mL). The organic layer is dried (magnesium sulfate), filtered and concentrated to give the title compound, NMR (300 MHz, CDCl$_3$) 7.75–7.3, 6.81, 6.75–6.6, 6.31, 4.90, 3.78–3.58, 3.22, 2.98, 2.88–2.45, 2.12–1.55, 1.46, 1.44, 1.12 and 0.88 δ.

PREPARATION 25
14α-Hydroxy-15,16-dehydro-17-ketomarcfortine A (Formula 9a)

To the crude 16-sulfoxyphenyl-15,16-dehydro-17-ketomarfortine A (Formula 23, PREPARATION 24, 13 g) in aqueous methanol (10/1, 300 mL) is added diethylamine (15 mL). After refluxing for 0.5 hr the reaction mixture is cooled to 20°–25°, diluted with water (450 mL), and extracted into methylene chloride (500 mL). Drying (magnesium sulfate), followed by concentration and chromatography (silica gel, 130 g; acetone/methylene chloride 30/70) the title compound.

PREPARATION 26
14α-Hydroxy-14β-vinylmarcfortine A (Formula 30)

A solution of 14-ketomarcfortine A (Formula 16, PREPARATION 15, 200 mg, 0.4 mmol) in THF (5 mL) at −78° is treated with a solution of vinylmagnesium bromide (1M, 4.0 mL, 4 mmol) in THF at −78°. The resulting mixture is stirred for 2 hr at −78° and warmed to 20°–25°. It is stirred at 20°–25° for 2 hr. The reaction is quenched by adding sodium carbonate (10%, 3 mL). The mixture is diluted with methylene chloride (30 mL), washed with saturated ammonium chloride solution, dried (magnesium sulfate) and concentrated. The residue is subjected to chromatography (silica gel; hexane/acetone, 6/4) to give the title compound, NMR (300 MHz, CDCl$_3$) 7.86, 6.78 & 6.67, 6.32, 6.58, 5.43, 5.18, 4.89, 3.7, 3.11, 2.95, 2.8–1.5, 1.44, 1.08 and 0.82 δ; MS (FAB, M/Z, [M+H])=520.

PREPARATION 27
14α-Hydroxy-14β-methylmarcfortine A N-oxide (Formula 32)

A solution of 14α-hydroxymarcfoTtine A (PREPARATION 11, 30 mg) in methylene chloride (3 mL) is treated with m-chloroperoxybenzoic acid (20 mg) at 0°. After the mixture is stirred for 0.5 hR, then partitioned between aqueous sodium bicarbonate (5%, 10 mL) and methylene chloride (20 mL). The layers are separated and the aqueous layer extracted with methylene chloride (10 mL). The combined organic extracts are dried with magnesium sulfate, filtered, and evaporated under reduced pressure at 0°, treated with triethylamine (30 μL) and concentrated to produce the title compound, NMR (300 MHz, CD$_3$OD) 6.91 & 6.70, 6.36, 4.91, 4.08 & 3.76, 3.5–3.1, 3.12, 2.8–1.6, 1.46 & 1.44, 1.50 and 0.93 (s, 3H) δ.

PREPARATION 28
14α-Hydroxy-15α-methylmarcfortine A (Formula 35)

14α-Hydroxy-15α-methyl-17-ketomarcfortine A (PREPARATION 32, 90 mg, 0.18 mmol) is dissolved in THF (10 mL) and treated with borane dimethyl sulfide complex (12M, 0.18 mL) at 0°. The mixture is stirred for 2 hr at 0°, then methanol (0.4 mL) is added and stirred for an additional 1 hr. After the solvent is evaporated, the residue is subjected to chromatography (silica gel; acetone/methylene chloride, 30/70) to give the title compound, NMR (300 MHz, CDCl$_3$) 8.39, 6.79 & 6.70, 6.36, 4.91, 3.81, 3.67, 3.03, 3.11, 2.68 & 1.86, 2.7–1.2, 1.44, 1.02, 1.11 and 0.85 δ; HRMS (FAB, M/Z, [M+H]) calculated for C$_{29}$H$_{37}$N$_3$O$_5$+H=508.2811, measured=508.2840.

PREPARATION 29
14,17diketo-15α-methylmarcfortine A (Formula 36)

A solution of oxalyl chloride (40 μL) in anhydrous methylene chloride (5 mL) is treated with DMSO (45 μL) at −78°. The mixture is stirred for 1 hr at −78°. A solution of 14α-hydroxy-15α-methyl-17-ketomarcfortine A (PREPARATION 33, 27 mg) in methylene chloride (2 mL) is added dropwise. The reaction mixture is stirred 20 min at −78°. TEA (0.3 mL) is added to the reaction mixture which is allowed to warm to 20°–25° during 20 min. The mixture is partitioned between sodium carbonate (10%, 10 mL) and methylene chloride (10 mL). The organic layer is dried (magnesium sulfate) and concentrated. The residue is subjected to chromatography (silica gel; methanol/methylene chloride, 1/20) to give the title compound, HRMS (FAB, M/Z, [M+H]) calculated for $C_{28}H_{31}N_3O_6$+H=506.2291, measured=506.2280.

PREPARATION 30

14α-hydroxy-14β-methyl-15α-methyl-17-ketomarcfortine A (Formula 37)

A solution of 14,17-Diketo-15α-methylmarcfortine A (PREPARATION 29, 25 mg, 0.05 mmol) in methylene chloride (5 mL) at −78° is treated with a solution of methylmagnesium bromide (3M, 0.2 mL, 0.6 mmol) in ether at −78°. The resulting mixture is stirred for 0.5 hr at −78°. The reaction is quenched by adding sodium carbonate (10%, a few drops). The mixture is diluted with methylene chloride (10 mL), dried (magnesium sulfate) and concentrated. The residue is subjected to chromatography (silica gel; methanol/methylene chloride, 4/96) to give the title compound, NMR (300 MHz, $CDCl_3$) 8.13, 6.78, 6.70, 6.33, 4.91, 3.75, 3.16, 3.05, 2.78, 2.68–2.57, 2.42–2.0, 1.64, 1.45, 1.44, 1.11, 1.04 and 0.92 δ.

PREPARATION 31

14α-hydroxy-14β-methyl-15α-methylmarcfortine A (Formula 38)

14α-Hydroxy-14β-methyl-15α-methyl-17-ketomarcfortine A (PREPARATION 30, 15 mg, 0.028 mmol) is dissolved in THF (10 mL) and treated with borane dimethyl sulfide complex (10M, 0.02 mL) at 0°. The mixture is stirred for 2 hr at 0°, then methanol (0.4 mL) is added and stirred for an additional 1 hr. After the solvent is evaporated, the residue is subjected to chromatography (silica gel; acetone/methylene chloride, 30/70) to give the title compound, NMR (300 MHz, $CDCl_3$) 7.82, 6.79, 6.67, 20 6.33, 4.90, 3.65, 3.09, 2.98, 2.69, 2.60–2.22, 2.06, 1.87, 1.85–1.75, 1.44, 1.43, 1.10, 0.94, and 0.86 δ.

PREPARATION 32

14α-Hydroxy-15α-methyl-17-ketomarcfortine A (Formula 34)

A mixture of 14α-hydroxy-15,16-dehydro-17-ketomarcfortine A (Formula 9a, 300 mg) in THF (12 mL) is treated with a solution of methylmagnesium bromide (3M, 1.0 mL, 5 equiv.) at 20°–25°. The resulting mixture is refluxed for 1.5 hr then cooled to 20°–25°. The reaction is quenched by adding saturated ammonium chloride (3 mL). The mixture is diluted with methylene chloride (30 mL), washed with saturated ammonium chloride solution, dried over magnesium sulfate and concentrated. The concentrate is subjected to chromatography (silica gel; methanol/methylene chloride, 1/20) to give the title compound, NMR (300 MHz, $CDCl_3$) 7.90, 6.80 & 6.70, 6.32, 4.89, 4.36, 3.74, 3.20, 3.06, 2.78 & 2.10, 2.5–1.8, 1.46 & 1.44, 1.13, 1.12 and 0.88 δ.

Alternatively, the title compound can be prepared by using lithium dimethyl cuprate reagent. To copper iodide (0.4 g, 0.002 mol) in THF at 0° is added methyl lithium (1.4M, 9 mL, 0.013 mol) dropwise. The resulting mixture is stirred for 15 minuties then treated dropwise with 14α-hydroxy-15,16-dehydro-17-ketomarcfortine A (Formula 9a, 0.5 g, 0.001 mol) in THF (12 mL) at 0°. Following 15 minutes of stirring the mixture is quenched with saturated ammonium chloride (25 mL) and extracted into ethyl acetate (30 mL). The organic extract is dried over magnesium sulfate, filtered and concentrated to give crude material which is purified by a chromatotron (4 mm plate; methanol/methylene chloride, 4/96) to give the title compound.

PREPARATION 33

14,17-Diketo-l5α-methylmarcfortine A (Formula 36)

A mixture of oxalyl chloride (40 μL) in anhydrous methylene chloride (5 mL) is treated with DMSO (45 μL) is formed at −78°. The mixture is stirred for 1 hr at −78°. A solution of 14α-hydroxy-15α-methyl-17-ketomarcfortine A (PREPARATION 33, 27 mg) in methylene chloride (2 mL) is added dropwise. The reaction mixture is stirred 20 min at −78°. Triethylamine (0.3 mL) is added to the reaction mixture which is allowed to warm to 20°–25° during 20 min. The mixture is partitioned between sodium carbonate (10%, 10 mL) and methylene chloride (10 mL). The phases are separated and the organic layer is dried over magnesium sulfate and concentrated. The concentrate is subjected to chromatography (silica gel; methanol/methylene chloride, 1/20) to give the title compound, HRMS (FAB, M/Z, [M+H]) calculated for $C_{28}H_{31}N_3O_6$+H=506.2291, measured=506.2280.

PREPARATION 34

Preparation of N-(18a)-demethylparaherquamide A

The culture Penicillium paraherquei CMI 68220, supplied by the C.A.B. International Mycological Institute, Ferry Lane, Kew, London, England, is maintained on agar slants prepared from a medium comprising glucose (10 g), starch (20 g), "Bacto-Casitone" (Trade Mark, 5 g), yeast extract (5 g), calcium carbonate (1 g) and agar (20 g) made up to 1 litre with tap water and adjusted to pH=7.3 before autoclaving. An inoculum is prepared by washing a slant culture with sterile water (10 ml) into a 3 litre Fernbach Erlenmeyer flask containing a medium comprising glycerol (50 g), peptonised milk (5 g), lactic casein (10 g) and "Ardamine" (1 g, Trade Mark) made up to 1 litre with tap water and adjusted to pH=7.0. The inoculum is incubated at 28° on a rotary shaker with a 2.5 cm throw at 170 r.p.m. for 144 hr.

The total contents are then transferred to a 100 litre mechanically agitated vessel containing 70 litres of the same medium and incubated at 28° until the first signs of pellet formation. This second stage seed culture (10 litres) is used to inoculate a 2,000 litre mechanically agitated fermenter containing 1,200 litres of the same medium. The fermentation is maintained at 28° with aeration at 1,200 litres per minute and agitation at 250 r.p.m. and the addition of dilute sulphuric acid if necessary at such a rate to prevent the pH rising above 6.4. After 6 days the broth is filtered using a plate and frame press and the mycelium is discarded. The filtrate (1,600 litres) is pumped into ethyl acetate (800 l) and briefly stirred. After settling the aqueous layer is discarded and the organic extract is washed with saline (60 l) before concentrating to dryness. The residue is suspended in ethyl acetate (125 ml) and filtered. The filtrate is added slowly to petroleum ether (bp=40°–60°, 2 l) with stirring and the precipitate is recovered by filtration. The solid precipitate is then chromatographed on a column of silica gel (600 g, Merck "Kieselgel 60", Trade Mark, 230–400 mesh) eluting with dichloromethane containing an increasing proportion of ethyl acetate. Fractions rich in the desired compound elute when the solvent composition is approximately 1/1. Fractions containing the desired compound are combined and concentrated to dryness. The title compound is separated by preparative h.p.l.c. using a C-18 bonded phase column and eluting with water/methanol mixtures as known to those skilled in the art. The composition of the fractions collected is monitored by analytical h.p.l.c. using a Beckman Ultrasphere-ODS (Trade Mark) (5 μm) hplc column (4.6× 250 mm) eluting with a water-methanol linear gradient from 1/1 to 100% methanol over 30 minutes at a flow rate of 0.85 ml per minute and monitoring by ultraviolet absorbance at 230 nm. The appropriate fractions are pooled and concentrated to give the title compound.

EXAMPLE 1
24,25,26,27,28-Pentanormarcfortine A (II)

Marcfortine A (I, 8.5 g, 0.018 mol) is dissolved in formnic acid (95% pure, 100 mL). The mixture is stirred at 20°–25° for 16 hr. The volatile components are removed and the residue is redissolved in methanol (100 mL). The mixture is concentrated and the residue is purified by chromatography (silica gel; methanol/methylene chloride, 10/90) to give the title compound, selected NMR (300 MHz, $CDCl_3+CD_3OD$) 0.80, 1.09, 1.4–2.0, 2.2–2.8, 3.10, 3.87, 6.52 and 6.61 $\delta$; MS (FAB, m/z, [M t $H^+$])=412.

EXAMPLE 2
7-O-Prenyl-24,25,26,27,28-pentanormarcfortine A (III)

To 4-bromo-2-methyl-2-butene (1.0 mL, 8.7 mmol) and potassium iodide (1.44 g, 8.7 mmol) which had been stirred in acetone (40 mL) for 5 min is added potassium carbonate (1.6 g, 11.7 mmol) followed by 24,25,26,27,28-pentanormarcfortine A (II, EXAMPLE 1, 1.2 g, 0.0029 mol) dropwise in acetone/water (10 mL/6 mL). The reaction mixture is stirred for 0.25 hr, quenched with a saturated solution of sodium sulfite (100 mL), and extracted into ethyl acetate (100 mnL). The organic layer is dried over magnesum sulfate, filtered and concentrated under reduced pressure to give the title compound, NMR (400 MHz, $CDCl_3$) 7.90, 6.79, 6.57, 5.50, 4.49, 3.70, 3.10, 2.99, 2.66, 1.83, 2.55–2.5, 2.39, 2.29, 2.14, 1.95–1.30, 1.76, 1.61, 1.10 and 0.81 $\delta$.

EXAMPLE 3
7-O-(2',3'-epoxy-3'-methyl)butyl-24,25,26,27,28-pentanormarcfortine A (IV)

To 7-prenyl-24,25,26,27,28-pentanormarcfortine A (III, EXAMPLE 3, 1.4 g, 2.9 mmol) in methylene chloride (30 mL) at 20°–25° is added 3-chloroperbenzoic acid (2.4 g, 8.3 mmol) in one portion. Following 0.5 hr of stirring, sodium bisulfite (6 g, in 50 mL of water) is added and stirring is continued for 0.5 hr. The reaction is quenched with sodium bicarbonate (sat., 100 mL) and extracted into ethyl acetate (100 mL). The organic extract is separated and dried over magnesium sulfate, filtered and concentrated to give the title compound as a mixture of diastereomers which is used without any further purification, NMR (400 MHz, $CDCl_3$) 8.52, 8.44, 6.82, 6.59, 4.56–4.47, 3.92–3.84, 3.69, 3.26–3.14, 3.11, 3.01, 2.70–2.55, 3.39, 2.30, 2.15, 1.98–1.50, 1.41, 1.40–1.20, 1.10, 0.82 and 0.81 $\delta$.

EXAMPLE 4
25-Hydroxy-24,25-dihydromarcfortine A (V)

To 7-O-(2',3'-epoxy-3'-methyl)-butyl-24,25,26,27,28-penta-nor-marcfortine A (IV, 1.2 g, 2.4 mmol) in THF (30 mL) at 20°–25° under a nitrogen atmosphere is added tin (IV) chloride (0.2 mL) dropwise. After 0.25 hr of stirring the reaction is quenched with potassium fluoride (10% aqueous solution, 50 mL) and extracted into ethyl acetate (100 mL). The organic extract is separated and dried over magnesium sulfate, filtered and concentrated to give the tide compound as a mixture of diastereomers which is used without any further purification. Selected NMR (400 MHz, $CDCl_3$) 8.17, 7.87, 6.80–6.45, 4.40, 4.25, 4.05–3.90 and 3.15 $\delta$.

EXAMPLE 5
24,25-Dihydro-25-oxomarcfortine A (VI)

To oxalyl chloride (0.045 mL) in methylene chloride (5 mL) at −78° is added DMSO (0.06 mL) slowly dropwise in methylene chloride (1 mL). Following 0.25 hr of stirring at −78°, 25-hydroxy-24,25-dihydromarcfortine A (V, EXAMPLE 4, 60 mg, 0.12 mmol) is added dropwise in methylene chloride (1 mL). The reaction mixture is stirred for 0.25 hr, then quenched with TEA (0.25 mL) and stirred at 20°–25° for 0.25 hr. The reaction mixture is partitioned between sodium bicarbonate (sat., 25 mL) and ethyl acetate (25 mL). The organic extract is separated and dried over magnesium sulfate, filtered, concentrated and chromatographed (silica gel; methanol/methylene chloride (5/95) to give the title compound, NMR (400 MHz, $CDCl_3$) 7.45, 6.77, 6.64, 4.89, 3.70, 3.11, 3.02, 2.70, 1.85, 2.65, 2.40, 2.31, 2.15, 1.95–1.85, 1.80–1.0, 1.53, 1.51, 1.13 and 0.85 $\delta$; HRMS (FAB, M/Z [M+H]) calculated for $C_{28}H_{35}N_3O_5$+H= 494.2655, measured=494.2662.

EXAMPLE 6
24,25-Dihydro-25-methylenemarcfortine A (VII)

To methyltriphenylphosphonium bromide (70 mg, 0.2 mmol) in ether (5 mL) at 20°–25° is added n-butyllithium (1.6M in hexane, 0.13 mL, 0.2 mmol) dropwise. The resulting mixture is stirred for 5 min under a nitrogen atmosphere at 20°–25°, then treated dropwise with 24,25-dihydro-25-oxomarcfortine A (VI, EXAMPLE 5, 25 mg, 0.05 mmol) in THF (5 mL). The reaction mixture is stirred for 0.25 hr, quenched with water (25 mL) and extracted into ethyl acetate (25 mL). The organic extract is separated and dried over magnesium sulfate, filtered, concentrated and chromatographed (silica gel; acetone/hexane, 40/60) to give the title compound, NMR (400 MHz, $CDCl_3$) 7.67, 6.72, 6.47, 5.24, 5.08, 4.90, 4.77, 3.60, 2.30, 3.04, 2.96, 2.60 & 1.78, 2.58–2.52, 2.23, 2.08, 1.88–1.20, 1.44 & 1.42 and 1.10 & 0.80 $\delta$; HRMS (FAB, M/Z, [M+H]) calculated for $C_{29}H_{37}N_3O_4$+H=492.2862, measured=492.2858.

EXAMPLE 7
24,25-Epoxymarcfortine A (VIII)

A mixture of marcfortine A (I, 0.25 g, 0.5 mmol) and m-chloroperbenzoic acid (60% pure, 0.4 g, 1.4 mmol) is stirred for 16 hr in methylene chloride (25 mL). The reaction mixture is treated with sodium bisulfite (1.1 g in 15 mL water) stirred for 0.5 hr, quenched with sodium bicarbonate (sat., 100 mL) and extracted into methylene chloride (25 mL). The organic extract is dried over magnesium sulfate, filtered, concentrated and chromatographed (silica gel; acetone/methylene chloride, 40/60) to give the title compound as an inseparable mixture of diastereomers, selected NMR (400 MHz, $CDCl_3$) 8.01 & 7.86, 6.80 & 6.58, 5.36–5.30 & 3.00–2.97, 3.70, 3.12, 2.69 & 1.85 and 2.40 $\delta$.

EXAMPLE 8
24,25-dihydro-25-methyleneparaherquamide A (VII)

Following the general procedure of EXAMPLES 1–6 and making noncritical variations but starting with ppp A, the title compound is obtained.

EXAMPLE 9
14α-Hydroxy-14β-methyl-24,25-dihydro-25-methylenemarcfortine A (VII)

Following the general procedure of EXAMPLES 1–6 and making noncritical variations but starting with 14α-hydroxy-14β-methylmarcfortine A, the title compound is obtained.

EXAMPLE 10
14α-Hydroxy-15α-methyl-24,25-dihydro-25-methylenemarcfortine A (VII)

Following the general procedure of EXAMPLES 1–6 and making noncritical variations but starting with 14α-hydroxy-15α-methylmarcfortine A, the title compound is obtained.

EXAMPLE 11
24,25-epoxyparaherquamide A (VIII)

Following the general procedure of EXAMPLE 7 and making noncritical variations but starting with paraherquamide A, the title compound is obtained.

EXAMPLE 12
14α-Hydroxy-14α-methyl-24,25-epoxymarcfortine A (VIII)

Following the general procedure of EXAMPLE 7 and making noncritical variations but starting with 14α-hydroxy-14β-methylmarcfortine A, the title compound is obtained.

EXAMPLE 13
14α-Hydroxy-15α-methyl-24,25-epoxymarcfortine A (VIII)

Following the general procedure of EXAMPLE 7 and making noncritical variations but starting with 14α-hydroxy-15α-methylmarcfortine A, the title compound is obtained.

EXAMPLE 14
N-(18a)-demethyl-2-deoxoparaherquamide A

N-(18a)-demethylparaherquamide A prepared according to PREPARATION 34 (50 mg, 0.1 mmol) is dissolved in ethylene glycol dimethyl ether (glyme, 5 mL) and water (0.5 mL). This mixture is then treated with lithium borohydride (0.15 g, 6.9 mmol) and heated to reflux for 5 hr. The reaction mixture is quenched with saline (25 mL) and extracted into ethyl acetate. The organic phase is separated and dried over magnesium sulfate, filtered and concentrated. The concentrate is purified by silica gel chromatogaphy to give N-(18a)-demethyl-2-deoxoparaherquamide A.

CHART A

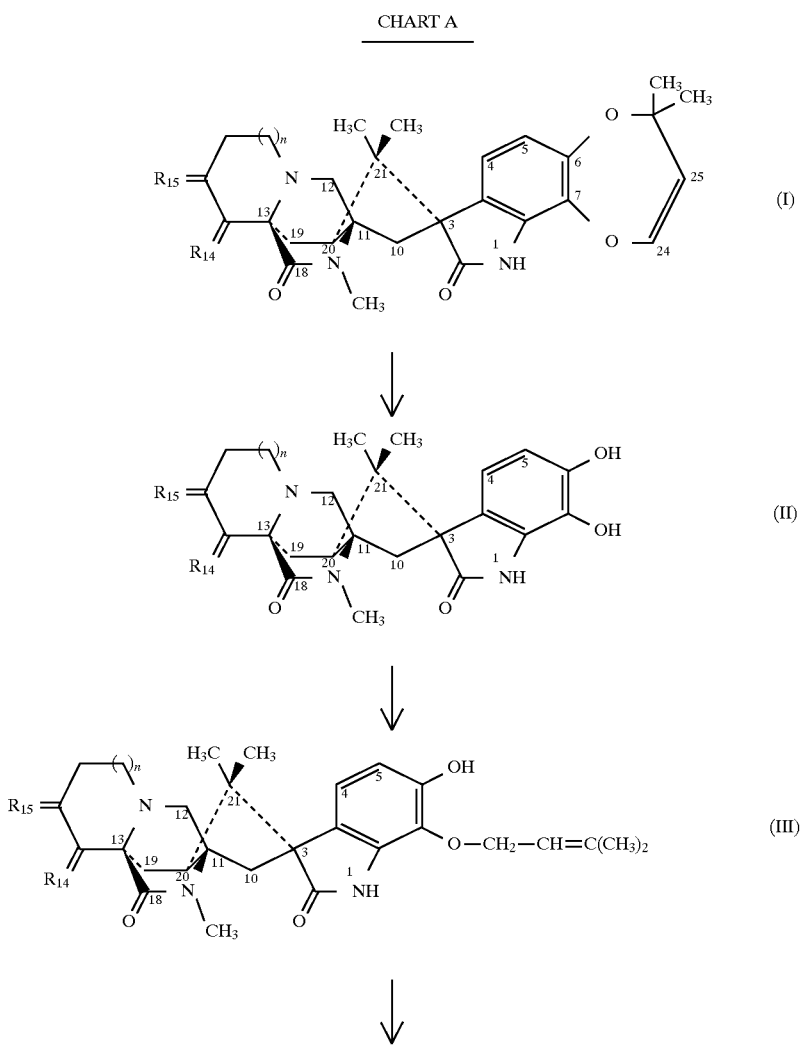

-continued
CHART A
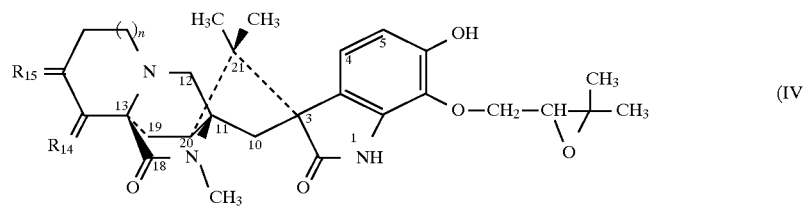
(IV)
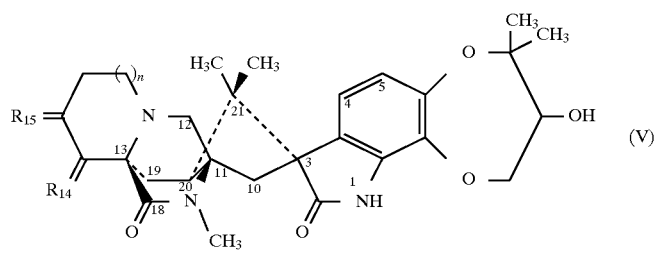
(V)
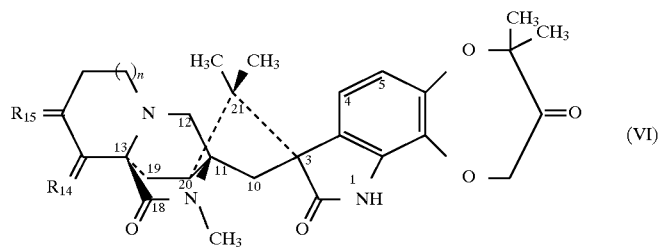
(VI)
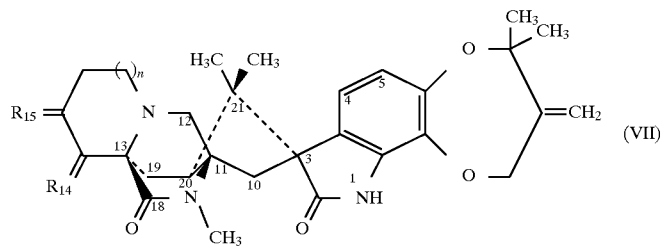
(VII)

CHART B (I)

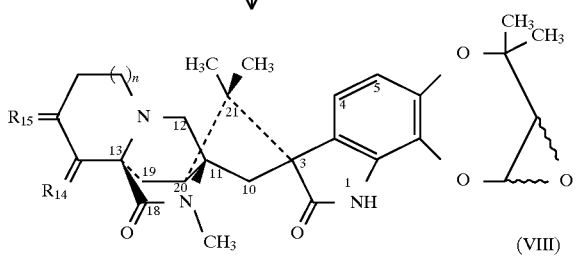

(VIII)

We claim:
1. 25-Methylene compounds of the formula (VII)

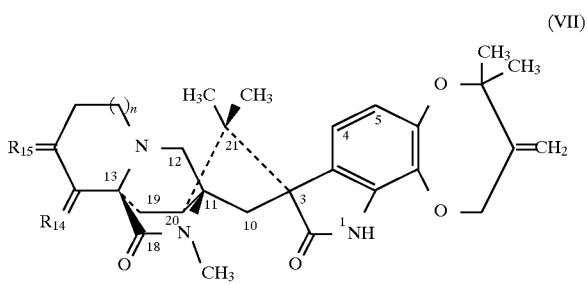

(VII)

where:
(I) Marefortine A
  (a) n is 1,
  (b) $R_{14}$ is $R_{14\alpha}:R_{14\beta}$ where $R_{14\alpha}$ is —H and $R_{14\beta}$ is —H,
  (c) $R_{15}$ is $R_{15\alpha}:R_{15\beta}$ where $R_{15\alpha}$ is —H and $R_{15\beta}$ is —H;
(II) Paraherquamide A
  (a) n is 0,
  (b) $R_{14}$ is $R_{14\alpha}:R_{14\beta}$ where $R_{14\alpha}$ is —OH and $R_{14\beta}$ is —CH$_3$,
  (c) $R_{15}$ is $R_{15\alpha}:R_{15\beta}$ where $R_{15\alpha}$ is —H and $R_{15\beta}$ is —H;
(III) 14-hydroxy-14-alkyl Marcfortine A
  (a) n is 1,
  (b) $R_{14}$ is $R_{14\alpha}:R_{14\beta}$ where $R_{14\alpha}$ is —OH and $R_{14\beta}$ is —C$_1$–C$_4$ alkyl,
  (c) $R_{15}$ is $R_{15\alpha}:R_{15\beta}$ where $R_{15\beta}$ is —H and $R_{15\beta}$ is —H;
(IV) 14-hydroxy-15-alkyl Marefortine A
  (a) n is 1,
  (b) $R_{14}$ is $R_{14\alpha}:R_{14\beta}$ where $R_{14\alpha}$ is —OH and $R_{14\beta}$ is —H,
  (c) $R_{15}$ is $R_{15\alpha}:R_{15\beta}$ where $R_{15\alpha}$ is C$_1$–C$_4$ alkyl and $R_{15\beta}$ is —H and pharmaceutically acceptable salts thereof.

2. Methylene compounds of formula (VII) according to claim 1 where the pharmaceutically acceptable salts are salts selected from the group consisting of the acids methanesulfonic, hydrochloric, hydrobromic, sulfuric, phosphoric, nitric, benzoic, citric, tartaric, fumaric, maleic, CH$_3$—(CH$_2$)m—COOH where m is 0 thru 4, HOOC—(CH$_2$)m—COOH where m is as defined above.

3. Methylene compounds of formula (VII) according to claim 1 where m, is 0.

4. Methylene compounds of formula (VII) according to claim 3 which is 24,25-dihydro-25-methyleneparaherquamide A.

5. Methylene compounds of formula (VII) according to claim 1 where m, is 1.

6. Methylene compounds of formula (VII) according to claim 5 which are selected from the group consisting of:
  24,25-dihydro-25-methylenemarcfortine A,
  14α-hydroxy-14β-methyl-24,25-dihydro-25-methylenemarcfortine A and
  14α-hydroxy-15α-methyl-24,25-dihydro-25-methylenemarcfortine A.

7. A methylene compound of formula (VII) according to claim 6 which is 24,25-dihydro-25-methylenemarcfortine A.

8. 24,25-Epoxy compounds of the formula (VIII)

(VIII)

where:
(I) Marcfortine A
  (a) n is 1,
  (b) $R_{14}$ is $R_{14\alpha}:R_{14\beta}$ where $R_{14\alpha}$ is —H and $R_{14\beta}$ is —H,
  (c) $R_{15}$ is $R_{15\alpha}:R_{15\beta}$ where $R_{15\alpha}$ is —H and $R_{15\beta}$ is —H;
(II) Paraherquamide A
  (a) n is 0,
  (b) $R_{14}$ is $R_{14\alpha}:R_{14\beta}$ where $R_{14\alpha}$ is —OH and $R_{14\beta}$ is —CH$_3$,
  (c) $R_{15}$ is $R_{15\alpha}:R_{15\beta}$ where $R_{15\alpha}$ is —H and $R_{15\beta}$ is —H;
(III) 14-hydroxy-14-alkyl Marcfortine A
  (a) n is 1,
  (b) $R_{14}$ is $R_{14\alpha}:R_{14\beta}$ where $R_{14\alpha}$ is —OH and $R_{14\beta}$ is C$_1$–C$_4$ alkyl,
  (c) $R_{15}$ is $R_{15\alpha}:R_{15\beta}$ where $R_{15\alpha}$ is —H and $R_{15\beta}$ is —H;
(IV) 14-hydroxy-15-alkyl Marcfortine A
  (a) n is 1,
  (b) $R_{14}$ is $R_{14\alpha}:R_{14\beta}$ where $R_{14\alpha}$ is —OH and $R_{14\beta}$ is —H,
  (c) $R_{15}$ is $R_{15\alpha}:R_{15\beta}$ where $R_{15\alpha}$ is C$_1$–C$_4$ alkyl and $R_{15\beta}$ is —H and pharmaceutically acceptable salts thereof.

9. 24,25-Epoxy compounds of formula (VIII) according to claim 8 where the pharmaceutically acceptable salts are salts selected from the group consisting of the acids methanesulfonic, hydrochloric, hydrobromic, sulfuric, phosphoric, nitric, benzoic, citric, tartaric, fumaric, maleic, CH$_3$—(CH$_2$)m—COOH where m is 0 thru 4, HOOC—(CH$_2$)m—COOH where m is as defined above.

10. 24,25-Epoxy compounds of formula (VIII) according to claim 8 where m is 0.

11. 24,25-Epoxy compounds of formula (VIII) according to claim 10 which is 24,25-epoxyparaherquamide A.

12. 24,25-Epoxy compounds of formula (VIII) according to claim 8 where m is 1.

13. 24,25-Epoxy compounds of formula (VIII) according to claim 12 which are selected from the group consisting of:

24,25-epoxymarcfortine A,

14α-hydroxy-14β-methyl-24,25-epoxymarcfortine A and

14α-hydroxy-15α-methyl-24,25-epoxymarcfortine A.

14. A 24,25-epoxy compound of formula (VII) according to claim 13 which is 24,25-epoxymarcfortine A.

* * * * *